United States Patent
O'Flynn et al.

(10) Patent No.: US 10,406,322 B2
(45) Date of Patent: Sep. 10, 2019

(54) CATHETER ASSEMBLIES HAVING A PROTECTIVE LUBRICIOUS SLEEVE

(71) Applicant: Hollister Incorporated, Libertyville, IL (US)

(72) Inventors: Padraig M. O'Flynn, Ballina (IE); Martin T. Moran, Galway (IE); Adam J. Foley, Swords (IE); James J. Fitzpatrick, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 436 days.

(21) Appl. No.: 15/105,182

(22) PCT Filed: Jan. 8, 2015

(86) PCT No.: PCT/US2015/010574
§ 371 (c)(1),
(2) Date: Jun. 16, 2016

(87) PCT Pub. No.: WO2015/105942
PCT Pub. Date: Jul. 16, 2015

(65) Prior Publication Data
US 2017/0056622 A1    Mar. 2, 2017

Related U.S. Application Data

(60) Provisional application No. 61/925,292, filed on Jan. 9, 2014.

(51) Int. Cl.
*A61M 25/00* (2006.01)
*A61M 25/01* (2006.01)

(52) U.S. Cl.
CPC ....... *A61M 25/0111* (2013.01); *A61M 25/002* (2013.01); *A61M 25/0017* (2013.01)

(58) Field of Classification Search
CPC ............ A61M 25/0017; A61M 25/002; A61M 25/0111
See application file for complete search history.

(56) References Cited

U.S. PATENT DOCUMENTS

| | | |
|---|---|---|
| 3,053,257 A | 9/1962 | Birtwell |
| 3,154,080 A | 10/1964 | Rowan et al. |

(Continued)

FOREIGN PATENT DOCUMENTS

| | | |
|---|---|---|
| WO | WO 9110466 A1 | 7/1991 |
| WO | WO 9638192 A1 | 12/1996 |

(Continued)

OTHER PUBLICATIONS

Notification of Transmittal of the International Search Report and the Written Opinion of the International Searching Authority for PCT/US2015/010574, dated May 12, 2015.

*Primary Examiner* — Kai H Weng
(74) *Attorney, Agent, or Firm* — Cook Alex Ltd.

(57) ABSTRACT

A catheter assembly includes a protective tip defining an interior chamber between its proximal and distal ends. A protective lubricious sleeve is positioned within the interior chamber. A catheter of the assembly is configured to be advanced proximally into and through the interior chamber to position at least a portion of the catheter within the protective sleeve, with the protective sleeve being retained upon the catheter as at least a proximal portion of the catheter exits the proximal end of the protective tip and is advanced through a body lumen. A second sleeve may be associated with the protective tip and configured to extend distally from the protective tip to remain outside of the body lumen during use and receive a more distal portion of the catheter.

20 Claims, 12 Drawing Sheets

(56) References Cited

U.S. PATENT DOCUMENTS

| | | | |
|---|---|---|---|
| 3,421,509 A | 1/1969 | Fiore | |
| 3,894,540 A | 7/1975 | Bonner, Jr. | |
| 3,902,500 A | 9/1975 | Dryden | |
| 4,062,363 A | 12/1977 | Bonner, Jr. | |
| 4,327,723 A | 5/1982 | Frankhouser | |
| 4,327,735 A | 5/1982 | Hampson | |
| 4,515,592 A | 5/1985 | Frankhouser | |
| 4,634,433 A | 1/1987 | Osborne | |
| 4,652,259 A * | 3/1987 | O'Neil | A61M 25/0111 600/581 |
| 4,655,214 A | 4/1987 | Linder | |
| 4,692,154 A * | 9/1987 | Singery | A61M 25/0111 604/172 |
| 4,767,409 A | 8/1988 | Brooks | |
| 5,098,379 A | 3/1992 | Conway et al. | |
| 5,209,726 A | 5/1993 | Goosen | |
| 5,234,411 A | 8/1993 | Vaillancourt | |
| 5,346,478 A | 9/1994 | Jinotti | |
| 5,749,357 A | 5/1998 | Linder | |
| 5,792,114 A | 8/1998 | Fiore | |
| 6,090,075 A | 7/2000 | House | |
| 6,217,569 B1 | 4/2001 | Fiore | |
| 6,471,684 B2 | 10/2002 | Dulak et al. | |
| 6,585,721 B2 | 7/2003 | Fiore | |
| 6,610,035 B2 | 8/2003 | Yang et al. | |
| 7,311,698 B2 | 12/2007 | Tanghoj et al. | |
| 7,601,158 B2 | 10/2009 | House | |
| 7,662,146 B2 | 2/2010 | House | |
| 7,789,873 B2 | 9/2010 | Kubalak et al. | |
| 7,918,831 B2 | 4/2011 | House | |
| 7,922,712 B2 | 4/2011 | Tanghoj et al. | |
| 8,011,505 B2 | 9/2011 | Murray et al. | |
| 8,282,624 B2 | 10/2012 | Tanghoej et al. | |
| 2003/0018302 A1 * | 1/2003 | Kavanagh | A61M 25/002 604/172 |
| 2005/0109648 A1 | 5/2005 | Kerzman et al. | |
| 2005/0197627 A1 | 9/2005 | Huang et al. | |
| 2006/0025753 A1 * | 2/2006 | Kubalak | A61M 25/0017 604/544 |
| 2007/0088330 A1 | 4/2007 | House | |
| 2007/0225649 A1 | 9/2007 | House | |
| 2008/0015527 A1 | 1/2008 | House | |
| 2008/0091145 A1 | 4/2008 | House | |
| 2008/0097411 A1 | 4/2008 | House | |
| 2008/0147049 A1 | 6/2008 | House et al. | |
| 2008/0171998 A1 | 7/2008 | House | |
| 2008/0172042 A1 * | 7/2008 | House | A61M 25/0111 604/544 |
| 2009/0018530 A1 | 1/2009 | Nielsen et al. | |
| 2009/0036874 A1 | 2/2009 | Horowitz et al. | |
| 2010/0030197 A1 | 2/2010 | House | |
| 2010/0145315 A1 | 6/2010 | House | |
| 2010/0198195 A1 | 8/2010 | Nishtala et al. | |
| 2010/0204682 A1 | 8/2010 | Tanghoj et al. | |
| 2012/0316515 A1 * | 12/2012 | Terry | A61M 25/002 604/257 |
| 2013/0281985 A1 * | 10/2013 | Querol Garcia | A61M 25/0032 604/540 |

FOREIGN PATENT DOCUMENTS

| | | |
|---|---|---|
| WO | WO 2005/014055 A2 | 2/2005 |
| WO | WO 2006 121508 A2 | 11/2006 |
| WO | WO 2013/130459 A1 | 9/2013 |

* cited by examiner

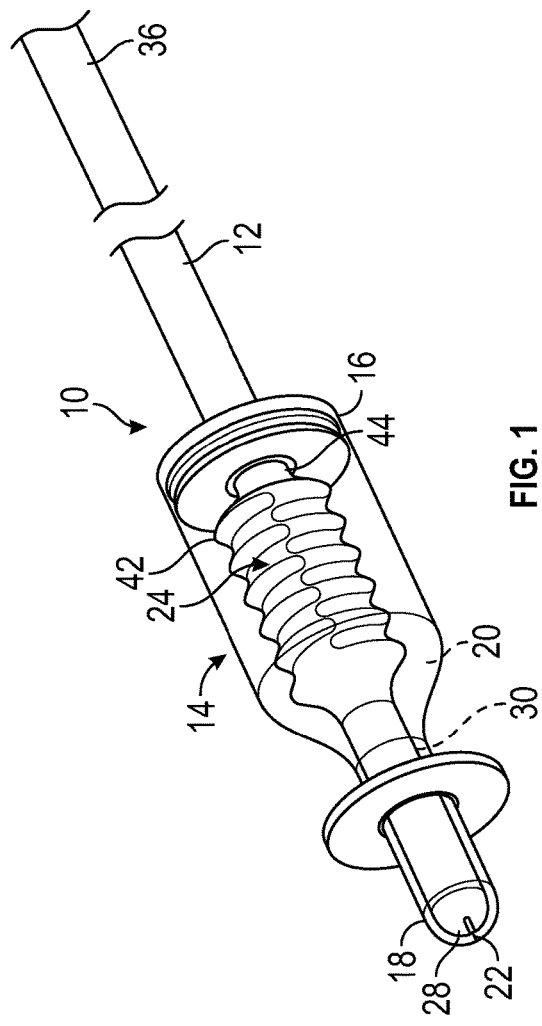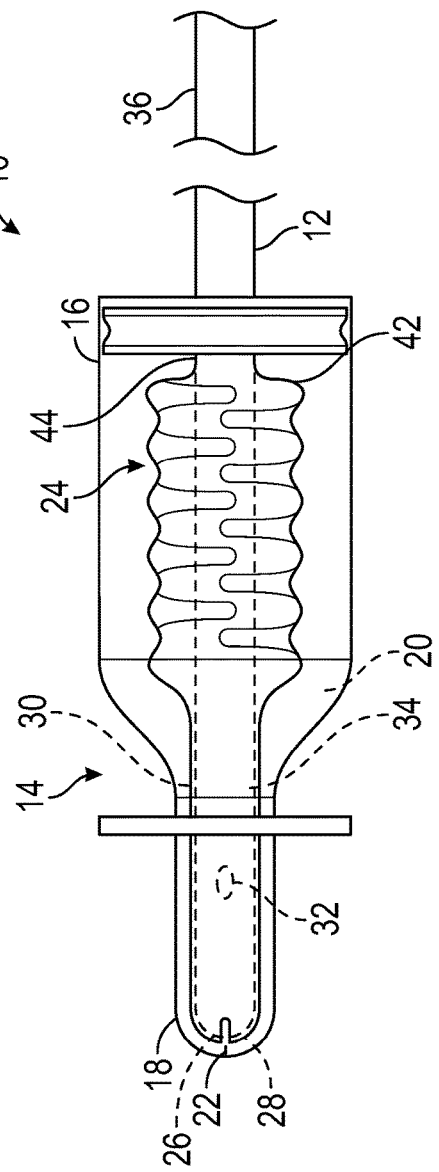

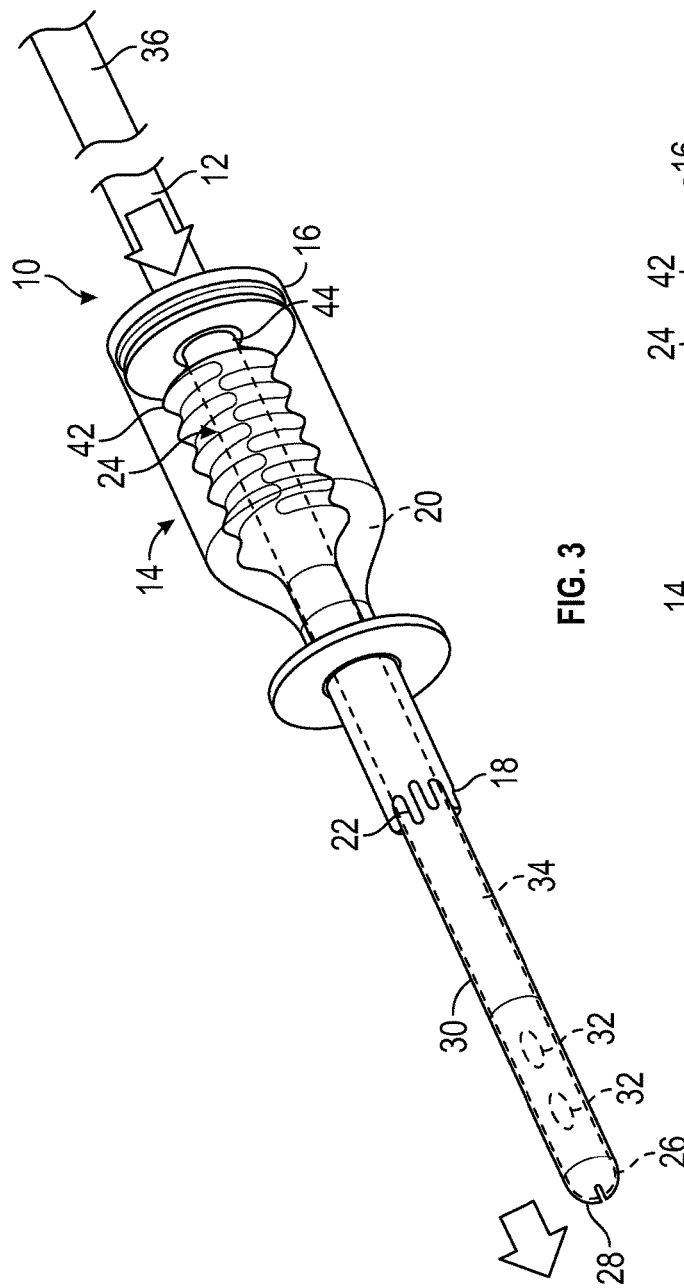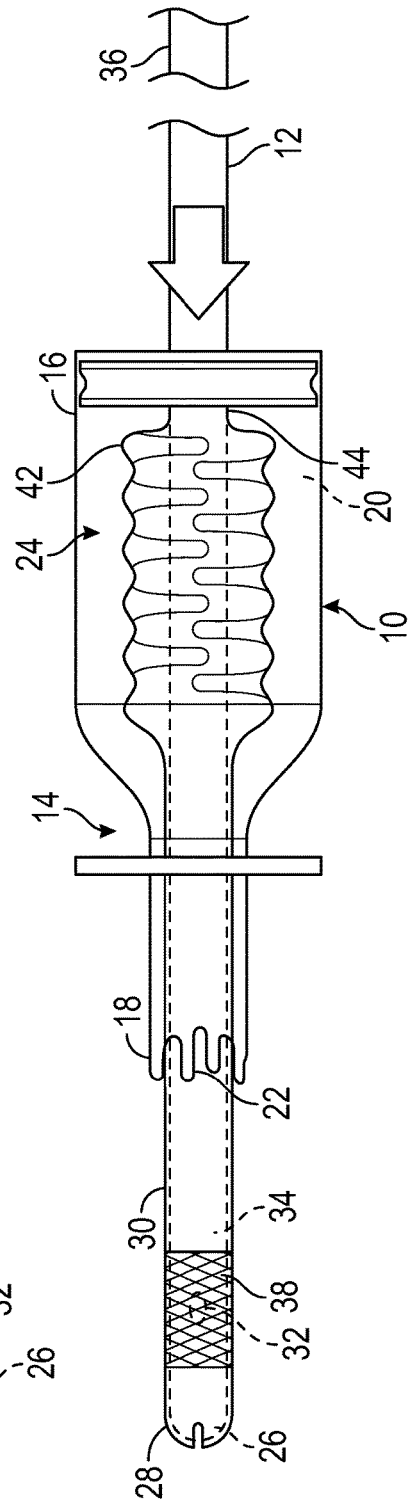

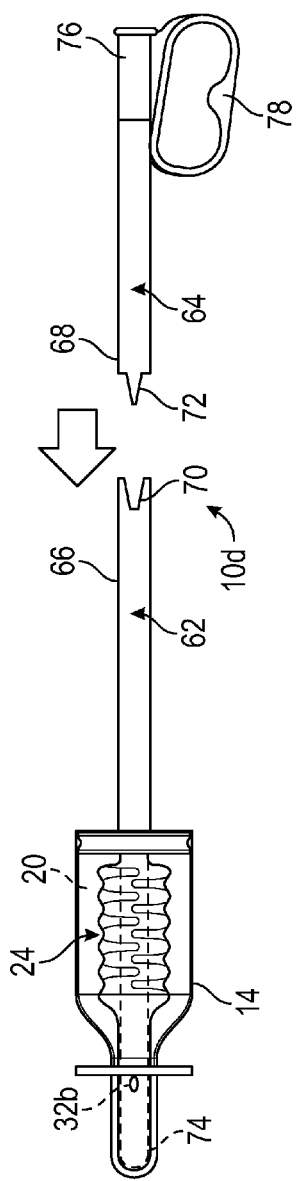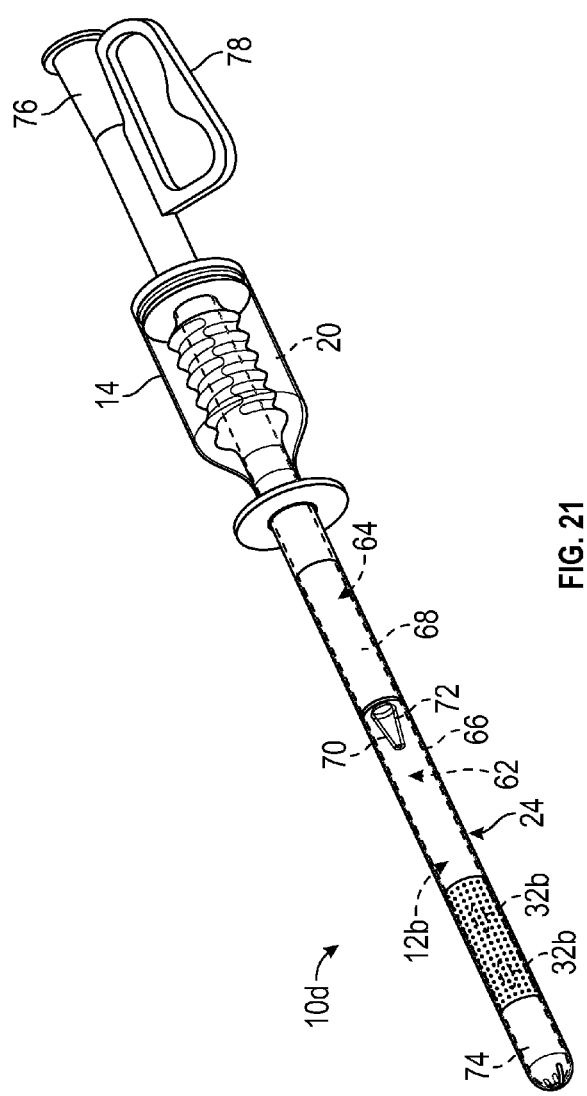

CATHETER ASSEMBLIES HAVING A PROTECTIVE LUBRICIOUS SLEEVE

RELATED APPLICATION

This application is a U.S. national stage application of PCT Patent Application Serial No. PCT/US2015/010574, filed Jan. 8, 2015, which claims the benefit of and priority of U.S. Provisional Patent Application Serial No. 61/925,292, filed Jan. 9, 2014, the contents of both of which are incorporated by reference herein.

DESCRIPTION

Technical Field

The present disclosure generally relates to catheters. More particularly, the present disclosure relates to catheters provided with a sleeve for lubrication and protection during insertion into a body lumen.

Background

Intermittent catheterization is a good option for many users who suffer from various abnormalities of the urinary system. Such catheters are typically provided as single use, individually packaged items and may include a gel-lubricant or hydrophilic coating that may be hydrated to act as a lubricant for reducing friction during insertion into the urethra.

Regarding gel-coated catheters, a user applies a gel-lubricant, such as a water-based gel-lubricant, to the surface of the catheter, which reduces friction for ease of insertion into the urethra. In some instances, the gel-lubricant is supplied with the packaged catheter, in which case the gel-lubricant may be applied to the catheter surface just before or during the packaging operation or as the catheter is being inserted by the user.

When a hydrophilic material is used as a lubricant, a thin coating of hydrophilic material is adhered to the outer surface of the catheter. When this coating is activated by swelling in contact with a hydrating liquid such as water, it provides a surface having an extremely low coefficient of friction. One form of this product provides a sterile, individually packaged, single-use catheter in a dry state or condition. The user opens the package, pours water into the package, waits 30 seconds, and then removes the catheter from the package, now ready for insertion. Other embodiments provide the amount of liquid water necessary for immersion of the catheter in a separate compartment of the package. In such embodiments, the user must open the separate compartment of the package to allow the liquid immersion water to enter the catheter-containing chamber for direct contact with the hydrophilic coated surface. The catheter is then removed from the package and inserted into the urethra. In yet another embodiment, the catheter is provided in a package that already contains enough loose liquid water to cause it to be immersed. In such an embodiment, the user simply opens the package and removes the catheter therefrom, and then inserts the catheter into the urethra, without the need to add water.

A disadvantage of the gel-coated and hydrophilic coated catheters described above is that the gel-lubricant may get on the hands of the user during handling or the immersion liquid may spill from the package as the user handles the catheter and tries to remove it for subsequent insertion.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a catheter assembly kit includes a protective tip defining an interior chamber between its proximal and distal ends. A protective lubricious sleeve is positioned within the interior chamber. A catheter of the kit is configured to be advanced proximally into and through the interior chamber to position at least a portion of the catheter within the protective sleeve, with the protective sleeve being retained upon the catheter as at least a proximal portion of the catheter exits the proximal end of the protective tip.

In another aspect, a method is provided for applying a protective lubricious sleeve to a catheter. The method includes providing a protective tip defining an interior chamber between proximal and distal ends of the protective tip, with a protective lubricious sleeve positioned within the interior chamber. At least a proximal portion of a catheter is advanced proximally into the interior chamber of the protective tip via the distal end of the protective tip. At least the proximal portion of the catheter is positioned within the sleeve as it is proximally advanced through the interior chamber. The proximal portion of the catheter is further proximally advanced out of the interior chamber via the proximal end of the protective tip, with the sleeve being retained on the catheter and a portion of the sleeve exiting the interior chamber with the proximal portion of the catheter.

In yet another aspect, a catheter assembly kit includes a protective tip with proximal and distal ends, with a protective lubricious sleeve secured to the protective tip. A catheter of the kit is configured to be advanced into contact with the protective sleeve for advancement through the protective tip from the distal end of the protective tip toward the proximal end of the protective tip to position at least a portion of the catheter within the protective sleeve, with the protective sleeve being retained upon the catheter as at least a proximal portion of the catheter exits the proximal end of the protective tip.

BRIEF DESCRIPTION OF THE DRAWINGS

FIG. 1 is a perspective view of a proximal portion of an embodiment of a catheter assembly according to an aspect of the present disclosure;

FIG. 2 is a side elevational view of the proximal portion of the catheter assembly of FIG. 1;

FIG. 3 is a perspective view of the proximal portion of the catheter assembly of FIG. 1, with a catheter thereof in a proximally advanced position;

FIG. 4 is a side elevational view of the proximal portion of the catheter assembly of FIG. 1, with a catheter thereof in a proximally advanced position;

FIG. 20 is a side elevational view of an alternative embodiment of a catheter assembly according to an aspect of the present disclosure;

FIG. 21 is a perspective view of the catheter assembly of FIG. 20, with a catheter thereof in an assembled, proximally advanced condition;

DETAILED DESCRIPTION OF THE ILLUSTRATED EMBODIMENTS

Figure 5:
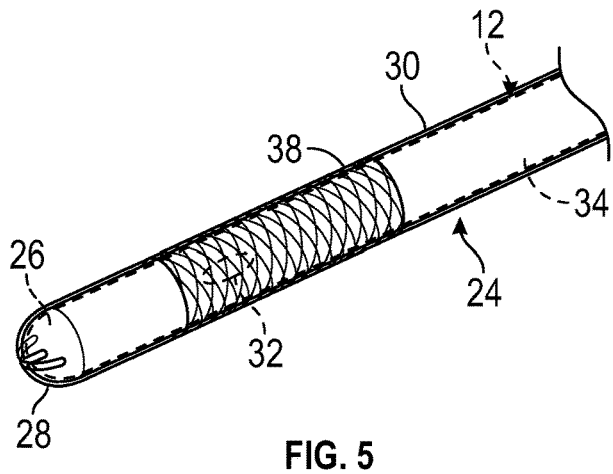
FIG. 5 is a perspective view of a proximal portion of a protective lubricious sleeve of the catheter assembly of FIG. 1.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIGS. 1-4 illustrate an embodiment of a catheter assembly 10, such as a urinary catheter assembly. The catheter assembly 10 may be variously configured without departing from the scope of the present disclosure, but in one embodiment, the catheter assembly 10 is provided as a kit, which includes a catheter 12 (such as an uncoated, polymeric urinary catheter) and a separate protective tip 14. The kit may include additional components (e.g., a fluid drainage bag or receptacle) without departing from the scope of the present disclosure.

The protective tip 14 extends between a distal end 16 and a proximal end 18, defining an interior chamber 20 therebetween. The proximal end 18 of the protective tip 14 may optionally be configured for insertion into a body lumen (e.g., a urethral opening) prior to advancement of the catheter 12 into the body lumen. The proximal end 18 of the protective tip 14 may include an aperture or opening 22 that may be moved between a closed configuration (in which there is no object positioned within the opening 22, as in FIGS. 1 and 2) and an open configuration (in which the catheter 12 or any other object is partially positioned within or extending through the opening 22, with a portion of the object positioned within the protective tip 14 and another portion positioned outside of the protective tip 14, as in FIGS. 3 and 4). In one embodiment, the proximal opening 22 is provided as a slit opening with one or more slits or cuts defining a plurality of deformable petals that may be moved to define the aforementioned open and closed configurations. In other embodiments, the opening 22 may be differently configured, provided that it is configured to allow passage of the catheter 12 therethrough. The distal end 16 of the protective tip 14 may also include an opening for passage of the catheter 12, with the opening at the distal end 16 being either movable from a closed configuration to an open configuration (similar to the proximal opening 22) or provided in always-open position.

A protective lubricious sleeve 24 is at least partially (but preferably completely) positioned within the interior chamber 20 of the protective tip 14. In use, the catheter 12 is advanced proximally into, through, and out of the interior chamber 20. As the catheter 12 moves into the interior chamber 20 via the distal opening of the protective tip 14, it enters into the interior of the sleeve 24. Further advancing the catheter 12 proximally through the interior chamber 20 causes the catheter 12 (typically the proximal end 26 of the catheter 12) to engage the sleeve 24 (typically the proximal end 28 of the sleeve 24), with the sleeve 24 being retained on the catheter 12. With the sleeve 24 retained on the catheter 12, further proximal advancement of the catheter 12 with respect to the protective tip 14 causes at least a proximal portion 30 of the sleeve 24 to exit the protective tip 14 with the proximal end 28 of the catheter 12 (FIGS. 3 and 4). In a preferred embodiment, the proximal end 18 of the protective tip 14 is positioned within a body lumen (e.g., a urethra) prior to advancement of the catheter 12 and sleeve 24 out of the protective tip 14.

The sleeve 24 provides a barrier which prevents bacteria on the catheter 12 from contacting a body lumen (e.g., a urethra) as the catheter 12 is advanced into and through the body lumen. Additionally, the sleeve 24 provides lubricity to aid catheter insertion. The sleeve 24 may be an inherently lubricious film or may have a lubricious coating applied thereto. For example, the sleeve 24 may be made from a hydrophilic polymer that becomes lubricious when wetted with a wetting agent or fluid. In such an embodiment, a wetting agent or fluid may be placed or located within the interior chamber 20 of the protective tip 14, as will be described in greater detail herein. Similarly, in embodiments in which the sleeve 24 has a lubricious coating, such as a gel-lubricant, the lubricant may be contained within the interior chamber 20 of the protective tip 14, with the coating being applied to the sleeve 24 when the sleeve 24 is placed into the protective tip 14. Alternatively, a sleeve 24 that is pre-coated with a lubricant may be positioned within the interior chamber 20 of the protective tip 14. By providing a sleeve 24 which covers the catheter 12 as it is advanced out of the protective tip 14, the catheter 12 may be uncoated or otherwise omit a lubricious coating and may be directly handled by a user without the risk of bacteria being transferred to the catheter 12 and then from the catheter 12 to the aforementioned body lumen. An uncoated, non-lubricous catheter 12 may be advantageous by being more readily gripped and manipulated than a lubricated catheter, thereby improving and simplifying catheter insertion.

The proximal end 28 of the sleeve 12 may be variously configured, depending on the configuration of the associated catheter 12. In one embodiment, the catheter 12 includes one or more side openings or eyes or drainage portions 32 at a proximal portion 34 of the catheter 12. The eyes 32 allow fluid (e.g., urine) to drain into and through the tubular catheter 12 from the proximal portion 34 of the catheter 12 to a distal portion 36 of the catheter 12, where it may exit the catheter 12 (e.g., via a funnel or opening). In one embodiment, which is shown in FIG. 5, the proximal end 28 of the sleeve 24 is closed to fully encircle and enclose the proximal end 26 and proximal portion 34 of the catheter 12. To allow drainage of fluid from a body location (e.g., the bladder) into and through the catheter 12, the sleeve 24 may include a mesh portion 38 configured to overlay at least a portion of the eyes 32 when the proximal end 26 of the catheter 12 is pressed against and/or adjacent to the proximal end 28 of the sleeve 24.

Figure 6:
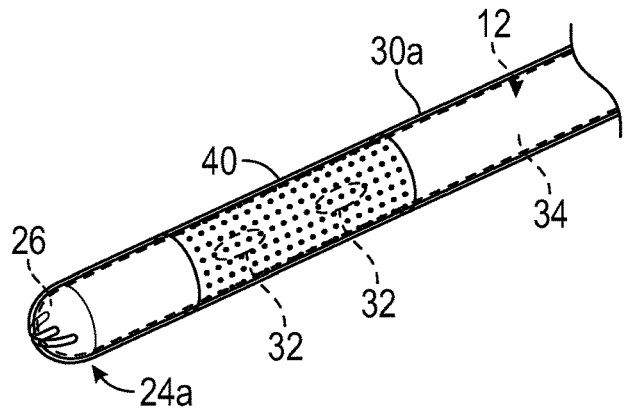
FIG. 6 is a perspective view of a proximal portion of another embodiment of a protective lubricious sleeve.

FIG. 6 shows a variation of the sleeve 24 of FIG. 5. In the embodiment of FIG. 6, the proximal portion 30a of the sleeve 24a includes a perforated portion 40, rather than a mesh portion 38. Other fluid-permeable portions besides a mesh or perforated portion (such as open portions having a size and shape similar to the catheter eyes 32) may also be incorporated into the proximal portion of protective lubricious sleeves according to the present disclosure.

Figure 7:
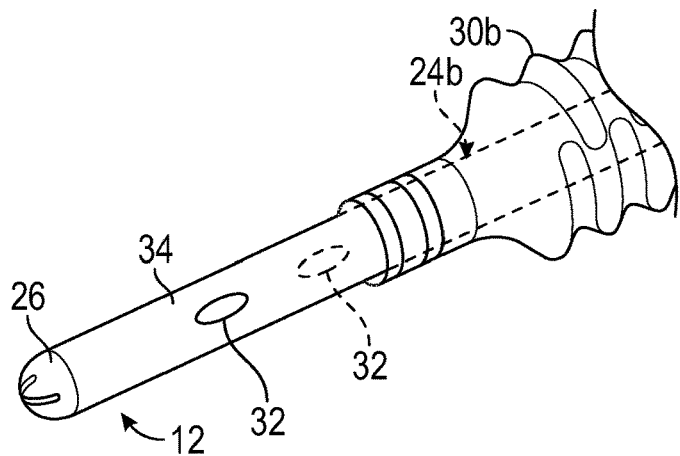
FIG. 7 is a perspective view of a proximal portion of yet another embodiment of a protective lubricious sleeve.

FIG. 7 illustrates another embodiment of a proximal portion 30b of a protective lubricious sleeve 24b. In the embodiment of FIG. 7, the sleeve 24b is configured to be retained upon the catheter 12 at only a portion distal of the eyes 32, such that the eyes 32 remain uncovered by the sleeve 24b. The sleeve 24b may either be configured to be retained upon the catheter 12 upon advancement of the catheter 12 through the protective tip 14 or may be secured (e.g., by a heat seal) to the catheter 12 during manufacturing. In embodiments such as FIG. 7, in which a proximal end 34 of the catheter 12 remains uncovered by the sleeve 24b, it may be advantageous for the proximal end 26 and uncovered portion of the catheter 12 to be lubricated to aid catheter insertion.

It should be understood that the illustrated sleeves are merely exemplary, and other protective lubricious sleeves may be provided without departing from the scope of the present disclosure. For example, in another embodiment, the proximal portion of a protective sleeve may be similar to the sleeves 24 and 24a of FIGS. 5 and 6 to the extent that it covers the entirety of the proximal end of the associated catheter 12, but omits any openings for allowing fluid to pass through the sleeve and enter into the catheter eyes 32. Instead, the sleeve may include a frangible or weakened portion that initially prevents fluid flow through the sleeve, but may be broken or otherwise manipulated to define an at least partially open configuration during use to allow fluid flow into the catheter eyes. In such an embodiment, the catheter and sleeve may be moved through a body lumen to a target location (e.g., moving through a male urethra until the proximal ends of the catheter and sleeve enter into the bladder), at which time the frangible portion may be broken (e.g., by distal relative movement of the sleeve with respect to the catheter) to define an opening or passage or otherwise allow fluid flow through or around the proximal end of the sleeve and into the catheter eyes. For example, the proximal end of the sleeve may have a weakened section, which may be punctured by the proximal end of the catheter upon proximal relative movement of the catheter with respect to the sleeve. In such a configuration, it may be advantageous for the catheter to have a greater length than the sleeve, to allow the catheter to be advanced farther into the body lumen than the sleeve, but with the sleeve having a particular minimum length (e.g., a length approximately equal to the length of the urethra).

In variations of the foregoing design, rather than including a frangible or weakened portion, the distal portion of the sleeve may be otherwise configured to change from a closed configuration to an at least partially open configuration during use to selectively allow fluid flow into the catheter eyes. For example, the proximal end of the sleeve may be defined by an elastic or deformable cuff or endpiece similar to the proximal end 28d of the sleeve 24d of FIGS. 15 and 16. By such a configuration, an opening defined in the elastic cuff overlays a closed portion of the catheter during advancement of the sleeve and catheter through a body lumen. When the proximal end of the catheter is in place, the sleeve may be moved distally with respect to the catheter, which causes the elastic cuff to deform and slide distally along the catheter until the opening is positioned distally of the catheter eyes. In this position, with the catheter eyes uncovered by the sleeve, fluid may flow into the catheter eyes and drained out of the body by the catheter. In other variations, perforated lines, peelable seals, and expandable perforations are among the variety of mechanisms that may be incorporated into a sleeve to allow a portion of its proximal end to fracture or otherwise move from a closed configuration to an at least partially open configuration.

Figure 8:
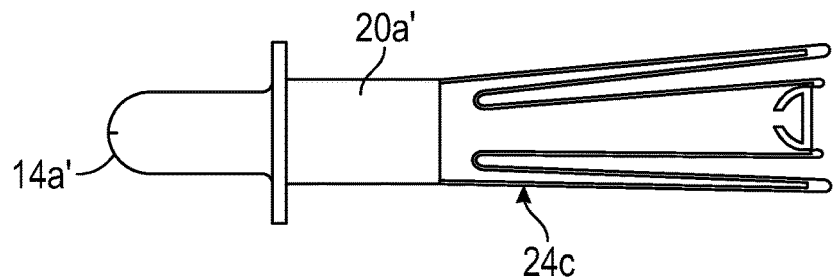
FIGS. 8 and 9 are side elevational views of a protective tip and protective lubricious sleeve of a catheter assembly according to an aspect of the present disclosure, with the sleeve in a folded configuration.
Figure 9:
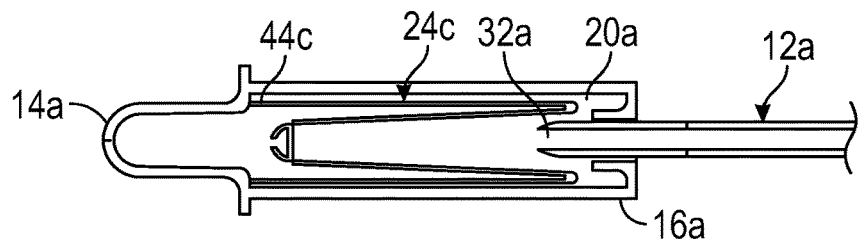

The sleeve 24 preferably has a greater length than the interior chamber 20, to allow the proximal portion 30 of the sleeve 24 to extend outside of the protective tip 14, while a distal portion 42 remains within the interior chamber 20 (as described above). Accordingly, the sleeve may be provided in a folded or bunched configuration. For example, FIG. 1 shows the sleeve 24 in a concertina-style formation within the interior chamber 20 so that the entire sleeve 24 may be positioned within the interior chamber 20. FIGS. 8 and 9 illustrate embodiments in which the sleeve 24c is provided in a folded configuration. In the embodiment of FIG. 9, the folded sleeve 24 is positioned within the interior chamber 20a of the protective tip 14a, whereas the protective tip 14a' of FIG. 8 omits an enclosed interior chamber. Instead, the distal portion 20a' of the protective tip 14a' of FIG. 9 is generally tubular, with an open distal end. The associated sleeve 24c may be secured to the open distal end of the protective tip 14a' or to any other suitable area of the distal portion 20a' of the protective tip 14a'. The sleeve 24c is inverted in the orientation shown in FIG. 8, with the lubricated surface of the sleeve 24c facing inwardly, such that the sleeve 24c may be handled without contacting the lubricant on the sleeve 24c. In use, the proximal end of the associated catheter is aligned with the proximal end of the sleeve 24c and advanced into and through the protective tip 14a', entering at the open distal end of the distal portion 20a'. As the sleeve 24c and catheter exit the proximal end of the protective tip 14a', the lubricated surface of the sleeve 24c (i.e., the surface facing inwardly in the orientation of FIG. 8) will be facing outwardly for advancement into and through a body lumen. Other configurations of the sleeve initially positioned either within the interior chamber of the protective tip or outside of the protective tip may also be practiced without departing from the scope of the present disclosure.

As for the distal end of the sleeve, it may be unsecured to the associated protective tip, but it may be preferred for the sleeve to be secured or connected to the protective tip. In the embodiment of FIGS. 1-4, the distal end 44 of the sleeve 24 is secured to the distal end 16 of the protective tip 14. In the embodiment of FIGS. 8 and 9, the distal end 44*c* is secured to a more proximal portion of the protective tip 14*a* (FIG. 9). These configurations are merely exemplary and, in other embodiments, a bunched sleeve 24 or a folded sleeve 24*c* may be secured to the associated protective tip 14, 14*a* at any suitable location.

Regardless of whether or not the sleeve is secured to the associated protective tip, the distal end of the sleeve may be open or openable, with the distal opening of the protective tip leading into the interior of the sleeve. By such a configuration, a catheter that is proximally advanced into the interior chamber of the protective tip via the distal opening of the protective tip will move into the interior of the sleeve for advancement of the catheter and sleeve into a body lumen, as described above.

Figure 10:
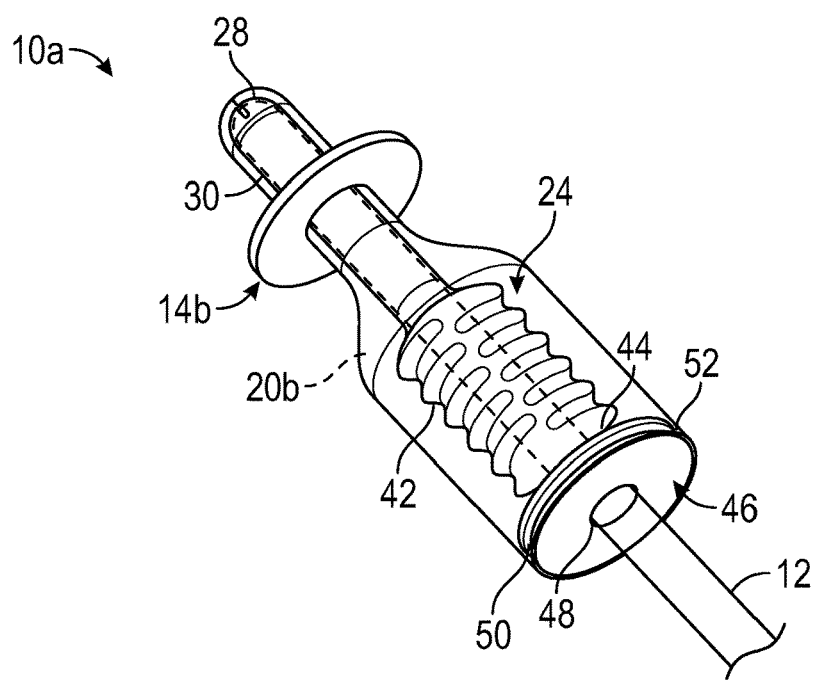
FIGS. 10 and 11 are perspective views of an alternative embodiment of a catheter assembly according to an aspect of the present disclosure.
Figure 11:
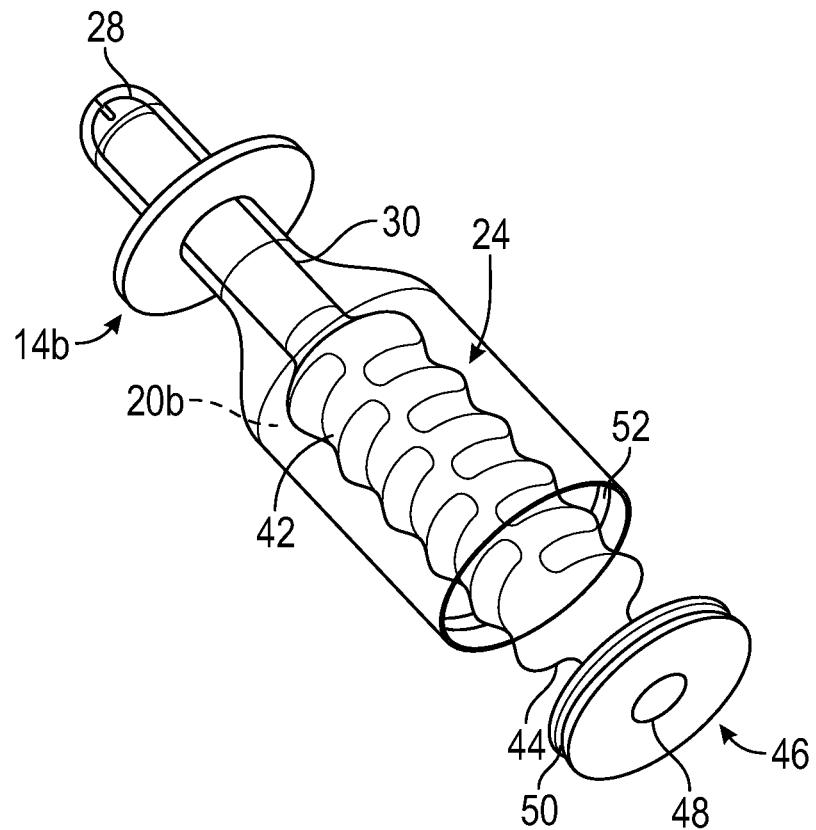
Figure 12:
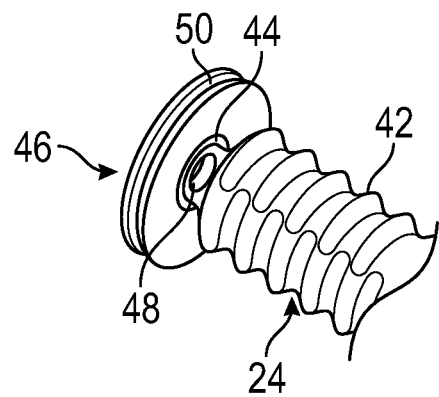
FIG. 12 is a detail view of an insert and a distal portion of a protective lubricious sleeve of the catheter assembly of FIGS. 10 and 11.

FIGS. 10-12 show an embodiment of a catheter assembly 10*a* in which the distal end of the protective tip 14*b* is defined by a separate grommet or insert 46, with the distal end 44 of the sleeve 24 being secured to the insert 46, such as by heat sealing. Such an embodiment may be preferred to an integrally formed or single-piece protective tip, in terms of ease of manufacturability, because it may be easier to position the sleeve 24 within the interior chamber 20*b* of the protective tip 14*b*.

FIG. 12 illustrates the proximal side of the insert 46, with the distal end 44 of the sleeve 24 being secured to the insert 46 around a central opening 48 of the insert 46, such that a catheter 12 being moved proximally into and through the insert opening 48 will pass into the interior of the sleeve 24.

The illustrated insert 46 is generally annular, with a groove or recess 50 along its outer perimeter. In such a configuration, the inner surface of the protective tip 14*b* may be provided with an inwardly extending, annular projection 52, which allows the insert 46 to be press-fit into place within the protective tip 14*b*, with the projection 52 being seated within the groove 50 to retain the insert 46. In other embodiments, the insert (if provided) may be differently configured and secured to the protective tip by different means without departing from the scope of the present disclosure. In general, it may be preferred for the insert to include a central opening to allow for passage of a catheter therethrough and into the interior of the sleeve, with an outer perimeter of the insert having a shape that matches the shape of the open distal end of the protective tip. It may be preferred for the shape of the perimeter of the insert to match the shape of the open distal end of the protective tip in order to provide a sterile seal between the protective tip and the insert. The insert may be fixedly or removably secured to the protective tip by any suitable means, such as a friction fit or an adhesive or the like.

Figure 13:
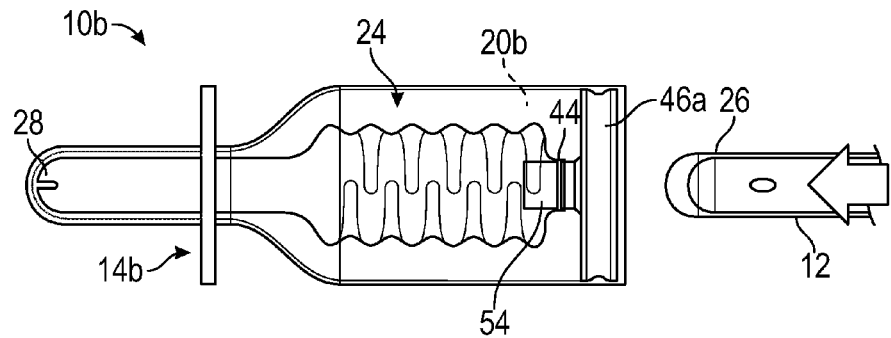
FIG. 13 is a side elevational view of an alternative embodiment of a catheter assembly according to an aspect of the present disclosure.
Figure 14:
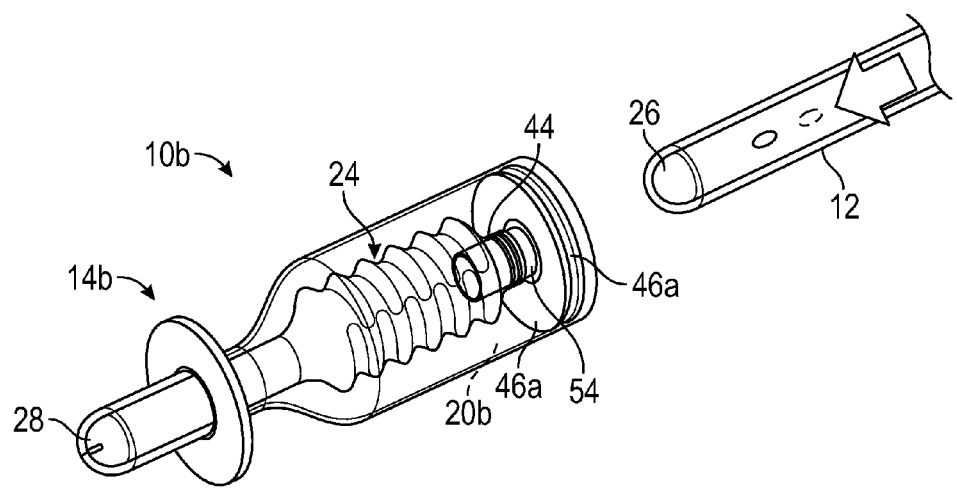
FIG. 14 is a perspective view of the catheter assembly of FIG. 13.

FIGS. 13 and 14 illustrate a catheter assembly 10*b* having the same catheter 12, protective tip 14*b*, and sleeve 24 as the embodiment of FIGS. 10 and 11, but a different insert 46*a*. In the embodiment of FIGS. 13 and 14, the proximal side of the insert 46*a* includes a generally tubular alignment barrel 54 surrounding the central opening 48. In this embodiment, the distal end 44 of the sleeve 24 may be secured to either the outer surface of the alignment barrel 54 (as illustrated) or to the proximal side of the insert 46*a*. The alignment barrel 54 helps to guide the proximal end 26 of the catheter 12 into the proximal end 28 and interior of the sleeve 24 as the catheter 12 is advanced into and through the interior chamber 20*b* of the protective tip 14*b*.

Figure 15:
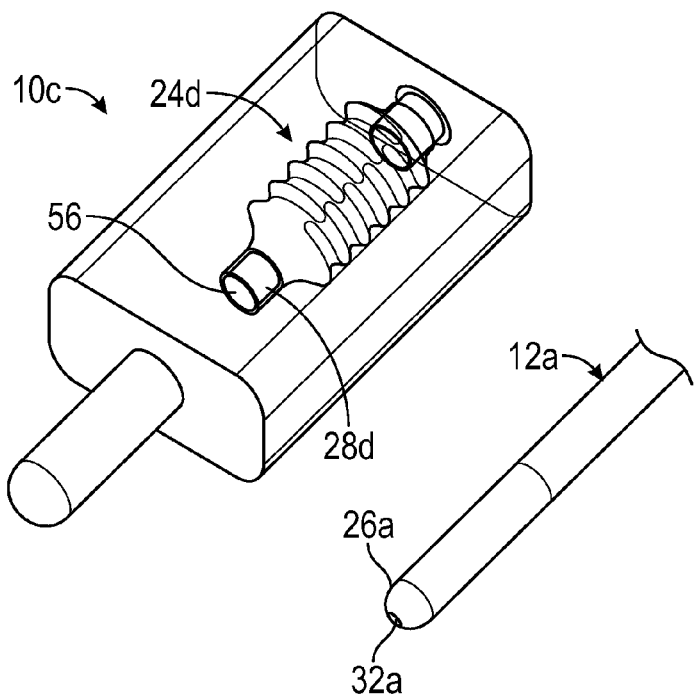
FIGS. 15 and 16 are perspective views of an alternative embodiment of a catheter assembly according to an aspect of the present disclosure.
Figure 16:
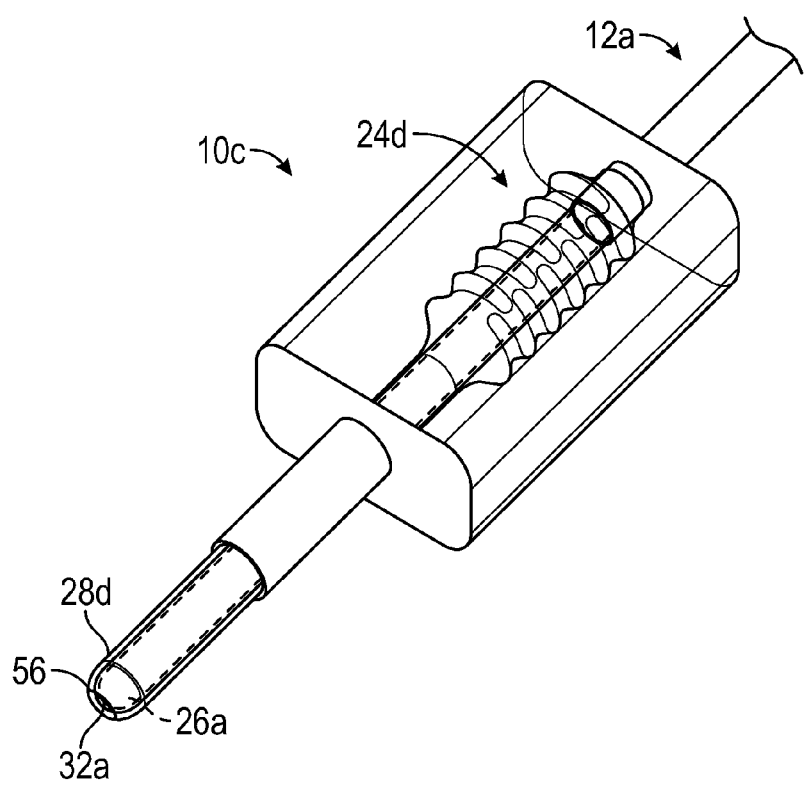

FIGS. 15 and 16 illustrate an embodiment of a catheter assembly 10*c* having an alternative catheter 12*a*. The catheter 12*a* of FIGS. 15 and 16 (also shown in FIG. 9) omits side openings or drainage portions, but instead includes an opening or eye or drainage portion 32*a* at its proximal end 26*a*. The associated sleeve 24*d* may also include an opening 56 at its proximal end 28*d* to become at least generally aligned with the eye 32*a* of the catheter 12*a* when the proximal end 26*a* of the catheter 12*a* is pressed against the proximal end 28*d* of the sleeve 24*d* (FIG. 16). In the illustrated embodiment, the proximal end 28*d* of the sleeve 24*d* is defined by an elastic or deformable cuff or endpiece that is separately formed and secured to the body of the sleeve 24*d*, but it is also within the scope of the present disclosure for the sleeve 24*d* to be formed as a single-piece device. Preferably, the sleeve opening 56 is larger than the catheter eye 32*a* so that the sleeve 24*d* does not obstruct the flow of fluid into the catheter 12*a* via the eye 32*a*, but it is also within the scope of the present disclosure for the sleeve opening 56 to be substantially the same size as or smaller than the catheter eye 32*a*. Alternatively, rather than a distal opening 56, the distal end 28*d* of the sleeve 24*d* may include a mesh portion or a perforated portion to allow fluid flow into the eye 32*a* at the proximal end 26*a* of the catheter 12*a*. Further, other fluid-permeable portions besides a mesh or perforated portion may also be incorporated into the proximal end 28*d* of the sleeve 24*d*.

Figure 17:
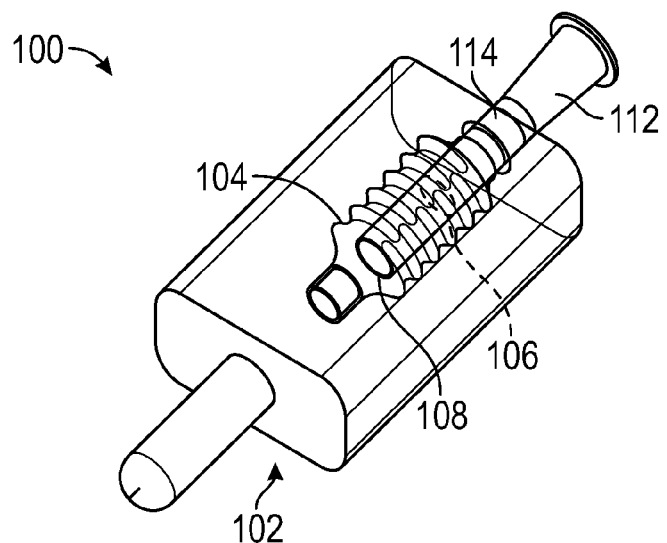
FIGS. 17 and 18 are perspective views of an alternative embodiment of a catheter assembly according to an aspect of the present disclosure.
Figure 18:
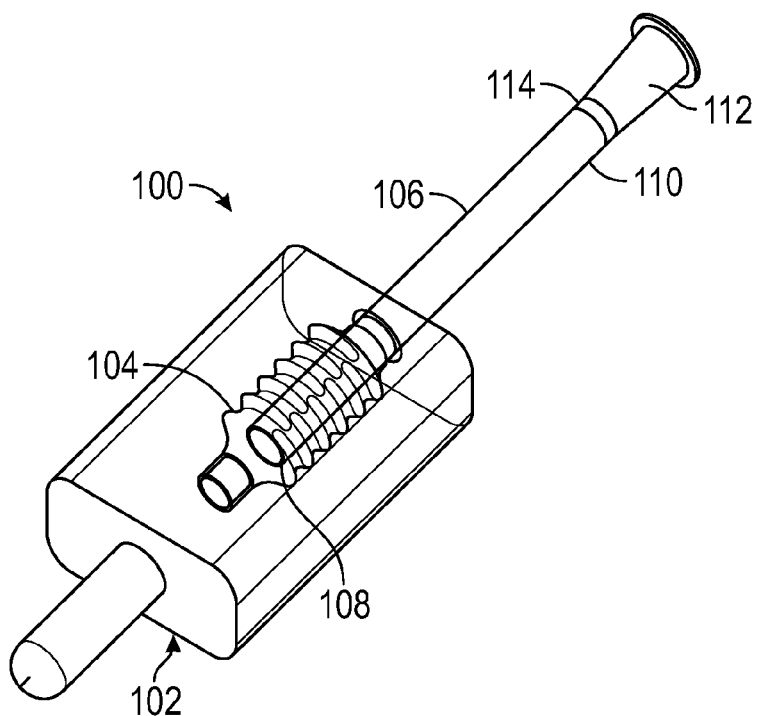

FIGS. 17 and 18 illustrate a catheter assembly 100 having a protective tip 102 of the type shown in FIGS. 13-16, with a catheter (not illustrated) and a sleeve 104 of the type shown in FIGS. 15 and 16. While the catheter assembly 100 of FIGS. 17 and 18 is provided with a catheter and sleeve 104 of the type shown in FIGS. 15 and 16 in a preferred embodiment, it is within the scope of the present disclosure for the catheter assembly 100 to have a differently configured catheter and/or sleeve, such as one of the various catheters and sleeves described herein.

The embodiment of FIGS. 17 and 18 further includes a distal or auxiliary sleeve 106, which may be provided as a flexible, deformable tubular body formed of a sheet or film material or the like. In contrast to the sleeve 104, the distal sleeve 106 is not configured to be advanced into the urethra, so the same considerations (e.g., lubricity) that affect the design of the sleeve 104 may have lesser importance when designing the distal sleeve 106. Accordingly, the material composition and/or surface treatment of the distal sleeve 106 may be different from composition and/or surface treatment of the sleeve 104. For example, the distal sleeve 106 may be handled by a user to manipulate a distal portion of the catheter during use of the catheter assembly 100, in which case it may be advantageous for the distal sleeve 106 to be non-lubricious. While the distal sleeve 106 may be formed of a different material and/or with a different surface treatment than the sleeve 104, it is also within the scope of the present disclosure for the distal sleeve 106 to be formed of the same material and/or with the same surface treatment as the sleeve 104.

The distal sleeve 106 is secured to the alignment barrel 108 (e.g., secured around the inner surface or perimeter of the alignment barrel 108) and/or to some other portion of the protective tip 102, with at least a portion of the distal sleeve 106 initially positioned within the alignment barrel 108, as in FIG. 17. Preferably, all or at least the majority of the distal sleeve 106 is initially positioned within the alignment barrel 108, but it is also within the scope of the present disclosure for less than half of the distal sleeve 106 to be initially positioned within the alignment barrel 108.

A portion of the distal sleeve 106 is distally advanced out of the alignment barrel 108, as shown in FIG. 18, to surround and receive the distal portion of an associated catheter, while the proximal portion of the catheter is positioned within the sleeve 104, as shown in FIG. 16. By such a configuration, the entire catheter may be received within the two sleeves 104 and 106, although it is also within the scope of the present disclosure for the proximal end and/or distal end of the catheter to be positioned outside of the sleeves 104 and 106.

The distal end 110 of the distal sleeve 106 may have a fluid drainage funnel 112 or comparable drainage device associated therewith, with the funnel 112 being used to drain fluid from a catheter positioned within the sleeves 104 and 106 into a toilet or other disposal location. If the distal sleeve 106 is provided with a funnel 112, then a simplified catheter omitting a funnel may be provided for use in combination with the protective tip 102. It may be advantageous for the funnel 112 and distal end of the catheter to be provided with mating formations, such that the funnel 112 may be press-fit onto the distal end of the catheter or otherwise secured in place with respect to the distal end of the catheter.

A proximal portion or end 114 of the funnel 112 may be initially fixed with respect to the protective tip 102 (e.g., with part or all of the proximal portion or end 114 received within the alignment barrel 108), as shown in FIG. 17. The funnel 112 may be gripped and pulled distally away from the protective tip 102 to move the distal sleeve 106 from the arrangement of FIG. 17 to the arrangement of FIG. 18. The distal sleeve 106 may be extended away from the protective tip 102 prior to the proximal end of a catheter being proximally advanced into the funnel 112, through the distal sleeve 106, and into the sleeve 104. Alternatively, the proximal end of a catheter may be proximally advanced into the funnel 112, through the distal sleeve 106 (positioned within the alignment barrel 108), and into the sleeve 104 prior to extending the distal sleeve 106 away from the protective tip 102. In either case, with the catheter positioned within the sleeves 104 and 106 (and the distal sleeve 106 in the extended arrangement of FIG. 18), the proximal end of the protective tip 102 may be positioned within the urethra and then the catheter may be advanced proximally out of the proximal end of the protective tip 102 and into the urethra. In another embodiment, the proximal end of the protective tip 102 may be positioned within the urethra prior to advancing the catheter into the funnel 112 and/or prior to moving the distal sleeve 106 into the extended arrangement of FIG. 18. The catheter may pinched or gripped through the distal sleeve 106 by the user to further advance the catheter through the urethra or, if the funnel 112 is secured to the distal end of the catheter, the funnel 112 may be gripped and moved proximally to further advance the catheter through the urethra. After use, the catheter may be disposed of or cleaned and reused, with the protective tip 102 preferably being discarded.

Figure 19:
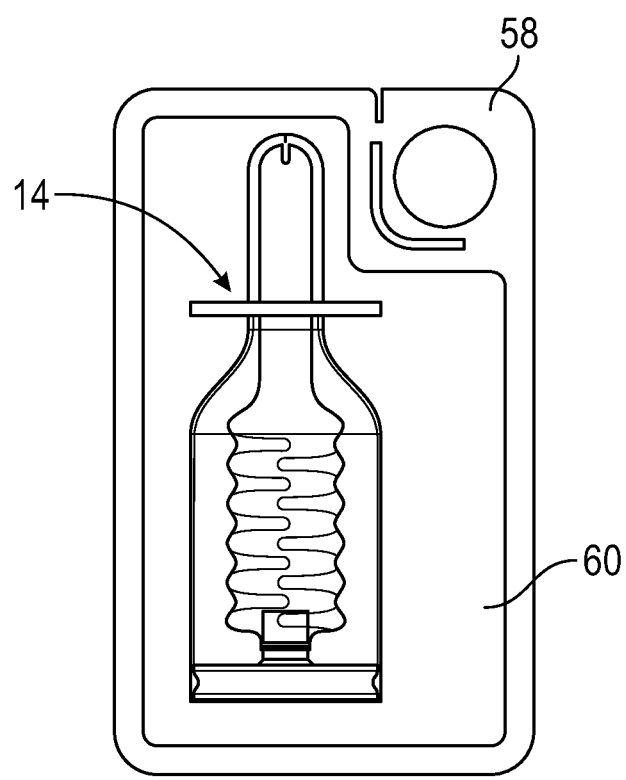
FIG. 19 is a front elevational view of a package containing a protective tip and protective lubricious sleeve of a catheter assembly kit.

In one embodiment, the catheter and protective tip are provided as separate components of a catheter assembly kit, which may be combined to define a catheter assembly. For example, FIG. 19 shows a protective tip 14 housed within a sealed package 58. The package 58 may include a frangible tear line 60 to allow a user to open the package 58 and remove the protective tip 14 for use with a separate catheter. When the protective tip 14 has been removed from the package 58, the proximal end of a catheter may be proximally advanced into and through the interior chamber of the protective tip 14, as described in detail above. After use, the entire catheter assembly may be discarded. Alternatively, one or more components of the catheter assembly may be reused. For example, the protective tip may be discarded after use, while the catheter may be reused (optionally after being washed, rinsed, or re-sterilized) with a new protective tip. Providing a reusable catheter may promote the use and provision of a catheter having more advanced features and functionality, as being able to reuse the catheter may render a more expensive catheter more cost-effective for users with budgetary restrictions.

In another embodiment, a catheter assembly kit may include a protective tip with the proximal end of a catheter pre-loaded into the interior chamber of the protective tip, inside the sleeve. FIGS. 20 and 21 illustrate one such embodiment of a catheter assembly 10d in which a portion of the catheter 12b is pre-loaded within the protective tip. In the embodiment of FIGS. 20 and 21, the catheter 12b includes separate proximal and distal members 62 and 64. The distal end 66 of the proximal member 62 and the proximal end 68 of the distal member 64 each include a fitting or connection point 70, 72 that is configured to mate with the fitting of the other member of the catheter 12b (FIG. 21). The fittings 70 and 72 may be variously configured, provided that they form a fluid passage between the proximal and distal members 62 and 64. Preferably, the fittings 70 and 72 are configured such that the proximal and distal catheter members 62 and 64 may be temporarily or removably connected to each other, but it is also within the scope of the present disclosure for the fittings 70 and 72 to fixedly secure the proximal and distal catheter members 62 and 64 together.

Prior to use, at least a proximal end 74 of the proximal member 62 may be pre-loaded within an interior chamber 20 of a protective tip 14 of the catheter assembly 10d, with at least the distal end 66 of the proximal member 62 positioned outside of the protective tip 14 (FIG. 20). The protective tip 14 and proximal catheter member 62 may be provided in a sealed package (similar to the package 58 of FIG. 19) prior to use. When the protective tip 14 and proximal catheter member 62 have been removed from the package (if provided), the distal catheter member 64 may be connected to the proximal member 62 using the fittings 70 and 72. With the catheter 12b fully assembled (as in FIG. 21), the catheter 12b may be proximally advanced to exit the interior chamber 20 of the protective tip 14, with the sleeve 24 retained upon the catheter 12b. After use, the entire catheter assembly 10d may be discarded. Alternatively, one or more components of the catheter assembly 10d may be reused. For example, the protective tip 14 and proximal catheter member 62 may be discarded after use, while the distal catheter member 64 may be reused (optionally after being washed, rinsed, or re-sterilized) with a new protective tip 14 and proximal catheter member 62.

The illustrated configuration of the proximal and distal catheter members 62 and 64 is merely exemplary, and the proximal and distal members 62 and 64 may be differently configured without departing from the scope of the present disclosure. For example, in the illustrated embodiment, the proximal member 62 includes side or lateral eyes 32b, but it is also within the scope of the present disclosure for the proximal member 62 to include a drainage eye at its distal end, as in the embodiment of FIGS. 15 and 16. Similarly, the distal member 64 is illustrated with a fluid drainage funnel 76 at its distal end and a gripping aid or handle 78 (which may be separate pieces or part of an integrated unit that is secured to the distal member 64), but either or both of those components could be omitted or additional components may be included (e.g., a fluid drainage bag or receptacle).

In one embodiment, the proximal and distal catheter members 62 and 64 are formed of different materials and/or have different stiffness. For example, it may be advantageous for the distal member 64 to have a greater stiffness or rigidity than the proximal member 62, because the proximal member 62 will often be required to traverse a relatively tortuous body lumen (e.g., a male urethra), whereas the distal member 64 traverses a shorter, less tortuous section of the body lumen, and the enhanced rigidity helps to advance the assembled catheter 12*b* through the body lumen. However, it is also within the scope of the present disclosure for the proximal and distal catheter members 62 and 64 to be formed of the same material and to have the same stiffness.

Figure 22:
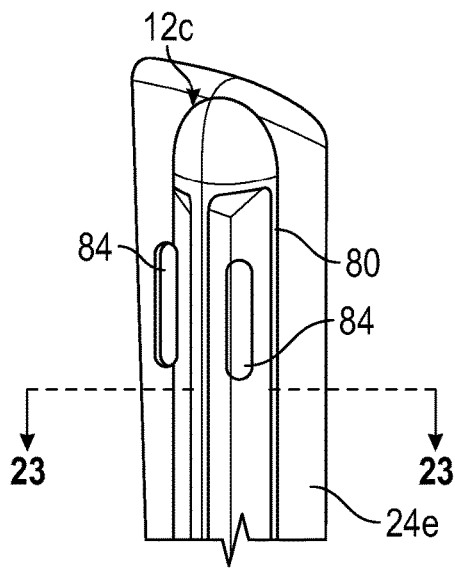
FIG. 22 is perspective view of a proximal portion of an alternative embodiment of a catheter and protective lubricious sleeve.
Figure 23:
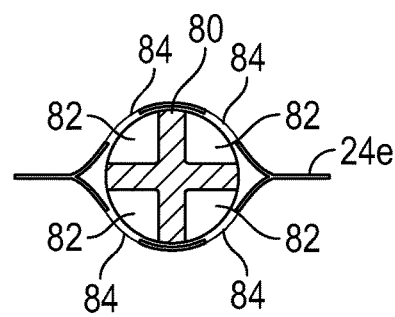
FIG. 23 is a cross-sectional view of the catheter and sleeve of FIG. 22, taken though line 23-23 of FIG. 22.
Figure 24:
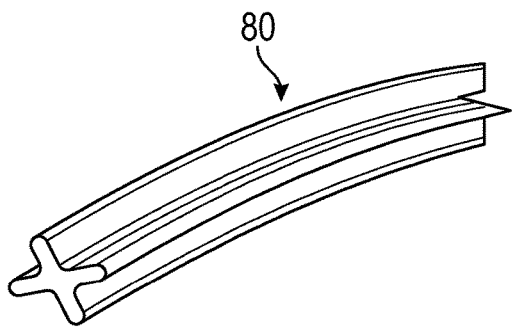
FIG. 24 is a perspective view of a portion of the catheter of FIG. 22.

FIGS. 22-24 illustrate yet another embodiment of a catheter 12*c* that may be incorporated into catheter assemblies of the present disclosure. In the illustrated embodiment, at least a portion 80 of the catheter 12*c* is non-tubular, but instead allows for fluid flow along one or more paths or drainage portions 82 defined between an outer surface of the non-tubular portion 80 and an inner surface of the associated protective lubricious sleeve 24*e* (FIG. 23). The non-tubular portion 80 of the catheter 12*c* may have any suitable cross-sectional shape, but in the illustrated embodiment has a generally cross- or X-shaped cross-section, which defines four external drainage portions 82. The sleeve 24*e* associated with the catheter 12*c* may include at least one fluid-permeable section 84 (e.g., an open section or a mesh or perforated section) to allow fluid flow into the interior of the sleeve 24*e*. Preferably, as shown in FIGS. 22 and 23, the sleeve 24*e* includes a plurality of fluid-permeable sections 84, with each drainage portion 82 having an associated fluid-permeable section 84 at least partially aligned therewith. A more distal section of the catheter 12*c* may be generally hollow or tubular, such that the fluid flowing through the external drainage portions 82 eventually enters into the interior of the catheter 12*c*, or the non-tubular portion 80 of the catheter 12*c* may extend to the distal end of the catheter 12*c*, such that fluid never enters into the interior of the catheter 12*c*.

Figure 25:
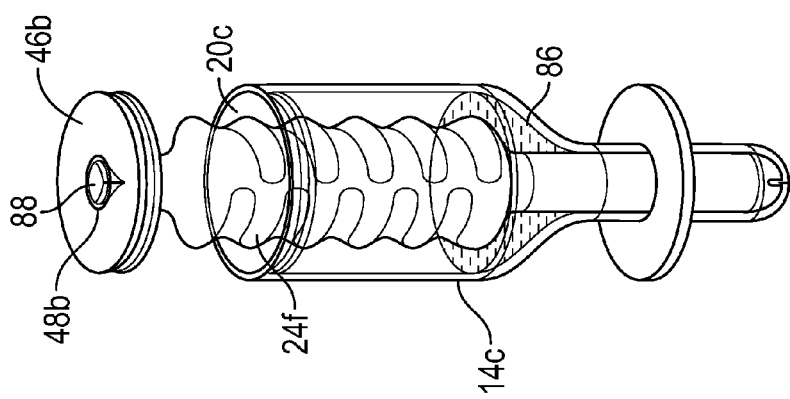
FIG. 25 is a perspective view of an alternative embodiment of a catheter assembly according to an aspect of the present disclosure.

As described above, the protective lubricious sleeve may be an inherently lubricious thin film or its lubricity may be provided by a coating, such as a gel-, water-, or oil-based layer. FIG. 25 illustrates an example of a protective tip 14*c* and sleeve 24*f* of a catheter assembly kit which employs a fluid lubricant for lubricating the sleeve 24*f*. The protective tip 14*c* of FIG. 25 is similar to the embodiment of FIGS. 10 and 11, except that a fluid lubricant 86 is placed into the interior chamber 20*c* of the protective tip 14*c* (surrounding the sleeve 24*f*) prior to securing the insert 46*b* to the protective tip 14*c*. The fluid lubricant 86 maintains the lubricity of the sleeve 24*f* for an extended period of time, allowing long-term storage of the catheter assembly kit prior to use. The lubricant may be a gel-type lubricant or, when the sleeve is formed of or includes a hydrophilic material, the lubricant may be a wetting agent or fluid, such as water or saline. The central opening 48*b* of the insert 46*b* may include a fluid-tight seal 88 (which may be similar to the opening at the proximal end of the protective tip) to prevent leakage of the fluid lubricant 86 out of the interior chamber 20*c*. The seal 88 may be pierceable or otherwise movable from a closed condition to an open condition to allow a catheter to pass proximally into and through the interior chamber 20*c*. Any other protective tip described herein may be provided with a fluid-tight seal, such as a fluid-tight seal 88 of the type shown in FIG. 25, at its distal end or incorporated into the associated insert.

Figure 26:
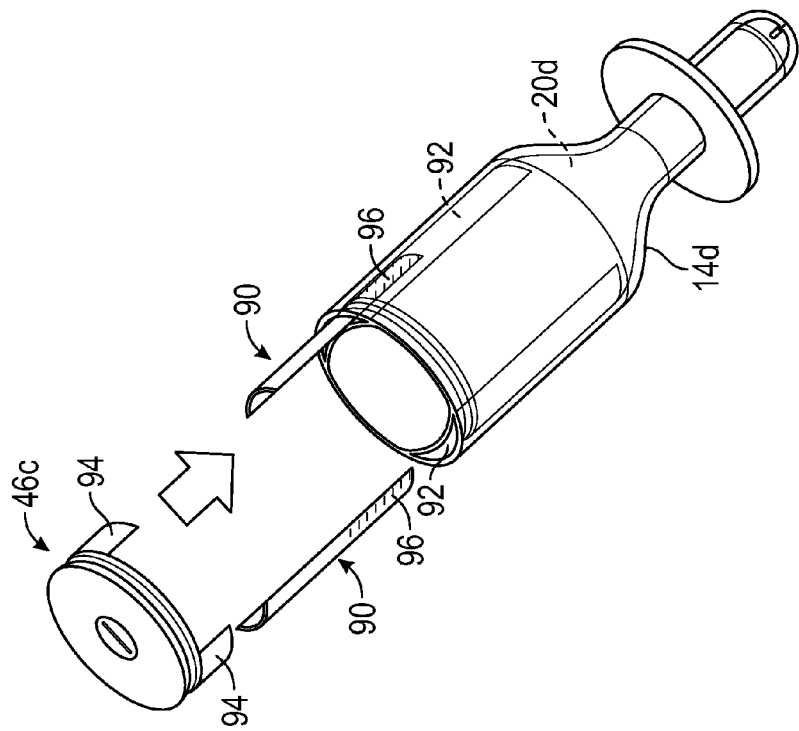
FIG. 26 is a perspective view of an alternative embodiment of a catheter assembly according to an aspect of the present disclosure.

In another embodiment, when the protective lubricious sleeve is formed of or includes a hydrophilic material, the sleeve may be wetted by one or more hydration sachets 90 positioned within the interior chamber 20*d* of the protective tip 14*d*, as in FIG. 26. In the illustrated embodiment, two substantially identical hydration sachets 90 are provided, with each inserted into a pocket 92 defined in or adjacent to the interior chamber 20*d* of the protective tip 14*d* prior to securing the associated insert 46*c* to the protective tip 14*d*. The insert 46*c* may include an extension 94 associated with each pocket 92, with each extension 94 configured to press the associated hydration sachet 90 into the pocket 92 and maintain the hydration sachet 90 therein. Each hydration sachet 90 contains a hydration substance 96 that acts to hydrate and lubricate the sleeve (not illustrated) within the interior chamber 20*d*, thus allowing long-term storage of the catheter assembly kit prior to use. In one embodiment, the hydration sachets may be fluid-containing pouches, with the pouches being formed of a water vapor-permeable, liquid-impermeable material, such as calcium carbonate. The hydration sachets 90 and associated pockets 92 and insert extensions 94 are illustrated as being elongated, with generally arcuate cross-sectional shapes, but it is within the scope of the present disclosure for the hydration sachets 90 and associated pockets 92 and insert extensions 94 to be otherwise configured.

Aspects of the present subject matter described above may be beneficial alone or in combination with one or more other aspects. Without limiting the foregoing description, in accordance with one aspect of the subject matter herein, there is provided a catheter assembly kit, which includes a protective tip defining an interior chamber between proximal and distal ends of the protective tip. A protective lubricious sleeve is positioned within the interior chamber. A catheter is configured to be advanced proximally into and through the interior chamber to position at least a portion of the catheter within the protective sleeve, with the protective sleeve being retained upon the catheter as at least a proximal portion of the catheter exits the proximal end of the protective tip.

In accordance with another aspect which may be used or combined with the preceding aspect, the distal end of the protective tip is defined by an insert defining a distal opening configured to allow proximal advancement of the catheter into the interior chamber, with a distal end of the sleeve being secured to the insert and the distal opening in communication with an interior of the sleeve.

In accordance with another aspect which may be used or combined with the preceding aspect, the insert includes a generally tubular alignment barrel surrounding the distal opening and positioned within the interior chamber and within the interior of the sleeve.

In accordance with another aspect which may be used or combined with the preceding aspect, the distal end of the sleeve is secured to an outer surface of the alignment barrel.

In accordance with another aspect which may be used or combined with the any of the preceding two aspects, at least a portion of a distal sleeve is positioned within the alignment barrel. At least a portion of the distal sleeve is configured to be advanced distally out of the alignment barrel to surround a distal portion of the catheter.

In accordance with another aspect which may be used or combined with the preceding aspect, a fluid drainage funnel is secured to the distal sleeve.

In accordance with another aspect which may be used or combined with the any of the preceding aspects, the catheter includes at least one drainage portion defined in a sidewall of the catheter.

In accordance with another aspect which may be used or combined with any of the first six aspects, the catheter includes at least one drainage portion defined in a proximal end of the catheter.

In accordance with another aspect which may be used or combined with any of the first six aspects, at least a portion of the catheter is substantially non-tubular, with a generally cross-shaped cross-section defining at least one drainage portion.

In accordance with another aspect which may be used or combined with any of the preceding three aspects, the sleeve includes a perforated portion configured to overlay at least a portion of the drainage portion as the proximal portion of the catheter exits the proximal end of the protective tip.

In accordance with another aspect which may be used or combined with any of the seventh through ninth aspects, the sleeve includes a mesh portion configured to overlay at least a portion of the drainage portion as the proximal portion of the catheter exits the proximal end of the protective tip.

In accordance with another aspect which may be used or combined with any of the seventh through eighth aspects, the sleeve is configured to be retained upon the catheter at only a portion distal of the drainage portion.

In accordance with another aspect which may be used or combined with the preceding aspect, the sleeve is heat-sealed to the catheter distally of the drainage portion, with the catheter being lubricated proximally of the location at which the sleeve is sealed to the catheter.

In accordance with another aspect which may be used or combined with any of the preceding aspects, the catheter comprises a proximal member and a separate distal member.

In accordance with another aspect which may be used or combined with the preceding aspect, at least a proximal end of the proximal member of the catheter is pre-loaded within the interior chamber and the sleeve, with at least a distal end of the proximal member of the catheter positioned outside of the interior chamber.

In accordance with another aspect which may be used or combined with any of the preceding two aspects, the proximal member of the catheter has a different stiffness than the distal member of the catheter.

In accordance with another aspect which may be used or combined with any of the preceding three aspects, the distal member of the catheter has a greater stiffness than the proximal member of the catheter.

In accordance with another aspect which may be used or combined with any of the preceding aspects, at least one hydration sachet is positioned within the interior chamber.

In accordance with another aspect which may be used or combined with any of the first seventeen aspects, a wetting agent and/or lubricant is positioned within the interior chamber, exteriorly of the sleeve.

In accordance with another aspect which may be used or combined with any of the preceding aspects, the sleeve is provided in a concertina-style formation within the interior chamber.

In accordance with another aspect which may be used or combined with any of the first nineteen aspects, the sleeve is provided in a folded formation within the interior chamber.

In accordance with another aspect, there is provided a method of applying a protective lubricious sleeve to a catheter. The method includes providing a protective tip defining an interior chamber between proximal and distal ends of the protective tip, with a protective lubricious sleeve positioned within the interior chamber. At least a proximal portion of the catheter is proximally advanced into the interior chamber of the protective tip via the distal end of the protective tip to position the proximal portion of the catheter within the sleeve. The proximal portion of the catheter is advanced out of the interior chamber via the proximal end of the protective tip, with the sleeve being retained on the catheter and a portion of the sleeve exiting the interior chamber with the proximal portion of the catheter.

In accordance with another aspect which may be used or combined with the preceding aspect, the protective tip is provided with a distal sleeve secured to it. At least a portion of the distal sleeve is distally advanced to surround a distal portion of the catheter.

In accordance with another aspect, there is provided a catheter assembly kit, which includes a protective tip having proximal and distal ends, with a protective lubricious sleeve secured to the protective tip. A catheter is configured to be advanced into contact with the protective sleeve for advancement through the protective tip from the distal end of the protective tip toward the proximal end of the protective tip to position at least a portion of the catheter within the protective sleeve, with the protective sleeve being retained upon the catheter as at least a proximal portion of the catheter exits the proximal end of the protective tip.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A catheter assembly kit, comprising:
   a protective tip defining an interior chamber between proximal and distal ends of the protective tip;
   a protective lubricious sleeve positioned within the interior chamber distally of the proximal end of the protective tip and secured at or adjacent to the distal end of the protective tip; and
   a catheter configured to be advanced proximally into and through the interior chamber to position at least a portion of the catheter within the sleeve, with the sleeve being retained upon the catheter for proximal movement of a portion of the sleeve out of the proximal end of the protective tip alone with at least a proximal portion of the catheter.

2. The catheter assembly kit of claim 1, wherein the distal end of the protective tip is defined by an insert defining a distal opening configured to allow proximal advancement of the catheter into the interior chamber, with a distal end of the sleeve secured to the insert and the distal opening in communication with an interior of the sleeve.

3. The catheter assembly kit of claim 2, wherein the insert includes a generally tubular alignment barrel surrounding the distal opening and positioned within the interior chamber and within the interior of the sleeve.

4. The catheter assembly kit of claim 3, further comprising a distal sleeve, wherein
   at least a portion of the distal sleeve is positioned within the alignment barrel, and
   at least a portion of the distal sleeve is configured to be advanced distally out of the alignment barrel to surround a distal portion of the catheter.

5. The catheter assembly kit of claim 4, further comprising a fluid drainage funnel secured to the distal sleeve.

6. The catheter assembly kit of claim 1, wherein the catheter includes at least one drainage portion defined in a sidewall of the catheter.

7. The catheter assembly kit of claim 1, wherein the catheter includes at least one drainage portion defined in a proximal end of the catheter.

8. The catheter assembly kit of claim 1, wherein at least a portion of the catheter is substantially non-tubular, with a generally cross-shaped cross-section defining at least one drainage portion.

9. The catheter assembly kit of claim 6, wherein the sleeve includes a perforated portion or a mesh portion configured to overlay at least a portion of said at least one drainage portion as said at least a proximal portion of the catheter exits the proximal end of the protective tip.

10. The catheter assembly kit of claim 6, wherein the sleeve is configured to be retained upon the catheter at only a portion distal of said at least one drainage portion.

11. The catheter assembly kit of claim 10, wherein the sleeve is heat-sealed to the catheter distally of said at least one drainage portion, with the catheter being lubricated proximally of a location at which the sleeve is sealed to the catheter.

12. The catheter assembly kit of claim 1, wherein the catheter comprises a proximal member and a separate distal member.

13. The catheter assembly kit of claim 12, wherein at least a proximal end of the proximal member of the catheter is pre-loaded within the interior chamber and the sleeve, with at least a distal end of the proximal member of the catheter positioned outside of the interior chamber.

14. The catheter assembly kit of claim 12, wherein the proximal member of the catheter has a different stiffness than the distal member of the catheter.

15. The catheter assembly kit of claim 12, wherein the distal member of the catheter has a greater stiffness than the proximal member of the catheter.

16. The catheter assembly kit of claim 1, further comprising a wetting agent and/or lubricant positioned within the interior chamber, exteriorly of the sleeve.

17. The catheter assembly kit of claim 1, wherein the sleeve is provided in a concertina-style formation or a folded formation within the interior chamber.

18. A method of applying a protective lubricious sleeve to a catheter, comprising:
providing a protective tip defining an interior chamber between proximal and distal ends of the protective tip, with a protective lubricious sleeve positioned within the interior chamber distally of the proximal end of the protective tip and secured at or adjacent to the distal end of the protective tip;
proximally advancing at least a proximal portion of a catheter into the interior chamber of the protective tip via the distal end of the protective tip;
positioning said at least the proximal portion of the catheter within the sleeve as the catheter is proximally advanced through the interior chamber; and
advancing said at least the proximal portion of the catheter out of the interior chamber via the proximal end of the protective tip, with the sleeve being retained on the catheter and a portion of the sleeve exiting the interior chamber with said at least the proximal portion of the catheter.

19. The method of claim 18, wherein said providing a protective tip includes providing the protective tip with a distal sleeve secured thereto, and further comprising distally advancing at least a portion of the distal sleeve to surround a distal portion of the catheter.

20. A catheter assembly kit, comprising:
a protective tip including proximal and distal ends;
a protective lubricious sleeve secured to the protective tip distally of the proximal end of the protective tip and secured at or adjacent to the distal end of the protective tip; and
a catheter configured to be advanced into contact with the sleeve for advancement through the protective tip from the distal end of the protective tip toward the proximal end of the protective tip to position at least a portion of the catheter within the sleeve, with the sleeve being retained upon the catheter for proximal movement of a portion of the sleeve out of the proximal end of the protective tip along with at least a proximal portion of the catheter.

* * * * *